United States Patent [19]

Knox

[11] Patent Number: 4,499,131
[45] Date of Patent: Feb. 12, 1985

[54] REUSABLE MOISTURE IMPERVIOUS UNDERPAD

[75] Inventor: Frank A. Knox, Urbana, Ill.

[73] Assignees: Albert Shelton; Verma Shelton, both of Urbana, Ill.

[21] Appl. No.: 476,033

[22] Filed: Mar. 17, 1983

[51] Int. Cl.³ .................... B32B 3/04; B32B 25/10
[52] U.S. Cl. .................... 428/68; 428/102; 428/126; 428/193; 428/267; 428/287; 5/484; 5/502
[58] Field of Search .............. 5/484, 502; 428/68, 428/286, 287, 126, 102, 193, 267, 128, 124

[56] References Cited

U.S. PATENT DOCUMENTS 3,427,670 2/1969 Nimoy .................... 5/484
4,278,719 7/1981 Sarnecki .................... 5/484

Primary Examiner—Alexander S. Thomas
Attorney, Agent, or Firm—Hill, Van Santen, Steadman & Simpson

[57] ABSTRACT

An underpad for use in a hospital-like setting is disclosed herein. In these situations it is desirable to minimize moisture or fluid penetration from one side of the pad to the other side, as for example, in situations where a patient may be incontinent. The pad can be repeatably washed and dried and includes at least two layers of materials secured to each other. One layer is a facing or fabric ply and the other layer comprises a moisture-resistant neoprene ply which resists degradation after repeated institutional washings and drying at temperatures on the order of 225° F.

2 Claims, 2 Drawing Figures

REUSABLE MOISTURE IMPERVIOUS UNDERPAD

BACKGROUND OF THE INVENTION

This invention relates to underpads, and in particular, to moisture-resistant pads of the type used in hospitals and other similar institutions.

Hospitals and other similar institutions place underpads between the patient and the bed or seat on which the patient is resting. These pads are moisture-resistant and intended to prevent moisture from the patient being absorbed by the bed or mattress. Such a pad is normally used as a precaution, but would be particularly important if the patient were incontinent.

There are two basic types of pads. One is made of a synthetic material and is disposable and used only once and thus is also comparatively expensive. The second type of pad is washable, which reduces the cost per use associated with the disposable pad. However, present reusable pads are unsatisfactory in that they degrade very rapidly upon washing and drying and are useful only a few times.

In the institutional washing required for such pads, they are washed in a bleach, alkali, and soap solutions at temperatures on the order of 160° F. The washing is followed by drying at temperatures on the order of 225° F.

When the present reusable pads are washed and dried at those temperatures, the moisture-resistant layers dry and crack, and thus lose their moisture-resisting ability. It has also been found that the moisture-resistant layers stick or adhere to the facing layers and become rigid and difficult to use.

It is therefore the object of this invention to provide a moisture-resistant underpad which can repeatedly withstand institutional washing and drying and very significantly reduce the cost per use.

These and other objects will become apparent from the following description and appended claims.

SUMMARY OF THE INVENTION

There is disclosed herein a moisture-resistant underpad which is repeatably washable and dryable. The pad includes at least two plies, a fabric face ply and a moisture-resistant neoprene-coated nylon ply. The plies are secured together and exhibit substantially no degradation after over two hundred institutional washings and drying at temperatures on the order of 225° F.

DESCRIPTION OF THE PREFERRED EMBODIMENT

Figure 1:
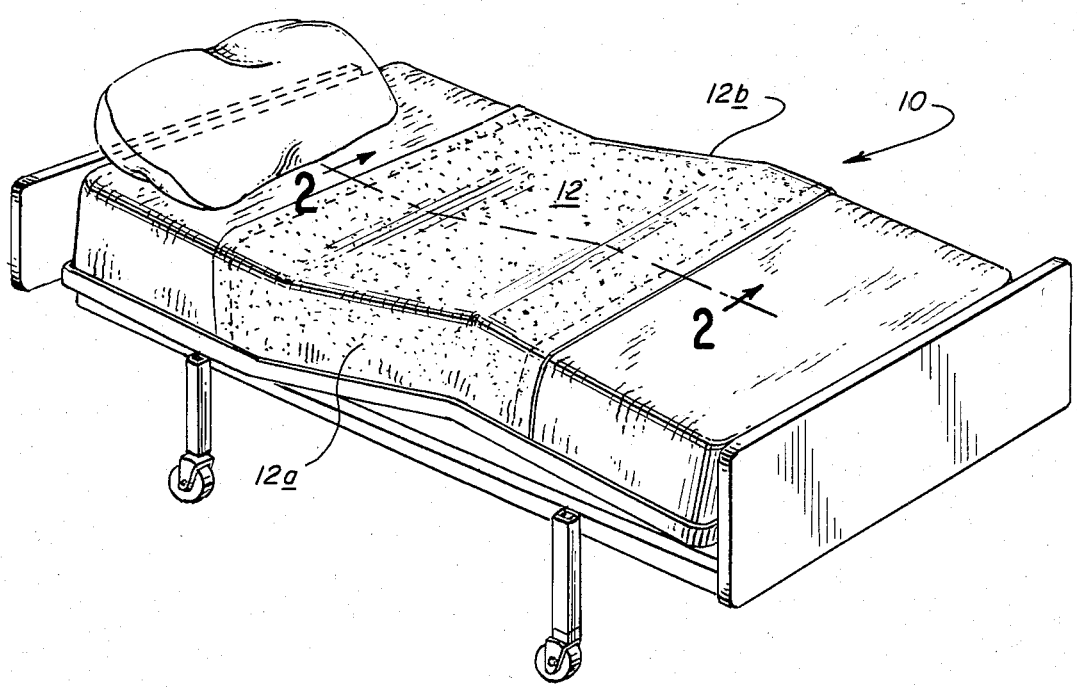
FIG. 1 is a perspective view showing a hospital bed with an underpad thereon.

Referring now to FIG. 1, there is shown a hospital bed 10 across which the underpad 12 has been placed. The pad has extended sides 12a and 12b, so that its edges can be tucked underneath the mattress and thus hold the pad in place on the bed.

Figure 2:
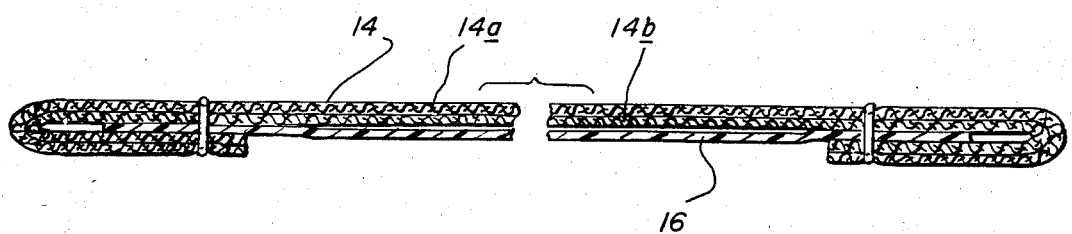
FIG. 2 is a cross-sectional view of the pad taken along line 2—2 of FIG. 1 showing the pad construction.

The pad 12, as shown in FIG. 2, includes a facing layer 14 on which the patient rests directly. In the preferred embodiment, the facing layer is made up of two plies 14a and 14b of double-thick cotton flannel.

The pad also includes the moisture-resistant ply 16 for positioning against the bed or mattress and which prevents moisture from the patient penetrating the pad and reaching the bed. The ply 16 is fabricated from a neoprene material which is identified as a rubber-coated nylon material. The rubber or neoprene layer is autoclavable, flame-resistant, and is 0.006 inches thick.

In order to form the pad, all of the plies are sewn together along about their periphery. Typically these pads are 32"×36" with 12" side extensions.

It has been found that these pads can be institutionally washed in bleach, alkali and soap solutions at about 160° F. and then dried at temperatures on the order of 225° F. Pads of the type described have been washed, dried, and effectively reused over two hundred (200) times.

It will be appreciated that numerous changes and modifications can be made to the embodiment shown herein without departing from the spirit and scope of this invention.

What is claimed and desired to be secured by Letters Patent of the United States is:

1. An underpad for use in situations where it is desirable to minimize moisture or fluid penetration from one side of the pad to the other side and which is repeatably washable and dryable said pad exhibiting substantial degradation resistance over two hundred (200) washing and drying operations, said pad comprising:

at least two layers of material secured to each other to form the pad;

one layer comprising a facing fabric ply which includes two plies of cotton flannel and the other layer comprising a moisture-resistant neoprene-coated nylon ply which resists degradation after repeated institutional washings and dryings at temperatures on the order of 225° F., said facing ply and said moisture-resistant ply layer secured to each other about the periphery of the pad, and said facing layer overlying the edge of said moisture-resistant layer so as to form a hem about the periphery of said pad.

2. An under pad as in claim 1, wherein said flannel is double-thick flannel.

* * * * *